ived_
United States Patent [19]

Graser et al.

[11] Patent Number: 5,955,656
[45] Date of Patent: Sep. 21, 1999

[54] MEASURING SENSOR

[75] Inventors: Theodor Graser; Gerhard Hoetzel; Johann Wehrmann; Heinz Eisenschmid, all of Stuttgart, Germany

[73] Assignee: Robert Bosch Gmbh, Stuttgart, Germany

[21] Appl. No.: 08/894,908

[22] PCT Filed: Nov. 19, 1996

[86] PCT No.: PCT/DE96/02201

§ 371 Date: Aug. 29, 1997

§ 102(e) Date: Aug. 29, 1997

[87] PCT Pub. No.: WO97/33164

PCT Pub. Date: Sep. 12, 1997

[30] Foreign Application Priority Data

Mar. 6, 1996 [DE] Germany .......................... 196 08 543

[51] Int. Cl.[6] .................................................. G01M 15/00
[52] U.S. Cl. ........................................ 73/23.31; 73/31.05
[58] Field of Search .............................. 73/23.31, 23.32, 73/31.05, 116, 117.2, 117.3, 118.1

[56] References Cited

U.S. PATENT DOCUMENTS

| Re. 33,980 | 6/1992 | Matsuura et al. ..................... 73/23.32 |
| 4,214,472 | 7/1980 | Maxwell et al. ...................... 73/23.31 |
| 4,225,842 | 9/1980 | Schlesselman et al. .............. 73/23.31 |
| 4,260,978 | 4/1981 | Yasuda et al. ........................ 73/31.05 |
| 4,308,518 | 12/1981 | Hattori et al. ........................ 73/23.31 |
| 4,309,897 | 1/1982 | Springer et al. ...................... 73/23.31 |
| 4,415,878 | 11/1983 | Novak .................................. 73/31.05 |
| 4,443,781 | 4/1984 | Ohta et al. ............................ 73/23.31 |
| 4,450,428 | 5/1984 | Ohta et al. ............................ 73/23.31 |
| 4,909,066 | 3/1990 | Matsuura et al. .................... 73/31.05 |
| 4,986,892 | 1/1991 | Kato et al. ........................... 204/427 |
| 5,031,445 | 7/1991 | Kato et al. ........................... 73/23.31 |
| 5,039,972 | 8/1991 | Kato et al. ........................... 73/31.05 |
| 5,329,806 | 7/1994 | McClanahan et al. ............... 73/31.05 |
| 5,467,636 | 11/1995 | Thompson et al. .................. 73/23.31 |
| 5,546,787 | 8/1996 | Hafele et al. ........................ 73/23.31 |
| 5,616,825 | 4/1997 | Achey et al. ........................ 73/23.31 |
| 5,739,414 | 4/1998 | Paulus et al. ........................ 73/23.31 |

FOREIGN PATENT DOCUMENTS 40 15486 11/1990 Germany .

*Primary Examiner*—George Dombroske
*Assistant Examiner*—Eric S. McCall
*Attorney, Agent, or Firm*—Venable; Norman N. Kunitz

[57] ABSTRACT

A measuring sensor, in particular for determining the oxygen content in exhaust gases of internal combustion engines, having a sensor element fixed in gastight fashion in a metal housing (14) and having a sealing flange (60) mounted on the housing (14) and resting on a sealing seat (76) embodied in an exhaust system (11). A union nut (80) is guided over onto the housing (14) and can be screwed into a thread (78) of an opening (70) provided in the exhaust system (11) and presses the sealing flange (60) against the sealing seat (76). The housing (14) has a housing part (12) on the side toward the gas to be measured and a further housing part (13) on the side toward the connection, and the sealing flange (60) is disposed on the housing part (13) on the side toward the connection and is shaped from the material of the housing part (13) on the side toward the connection.

4 Claims, 1 Drawing Sheet

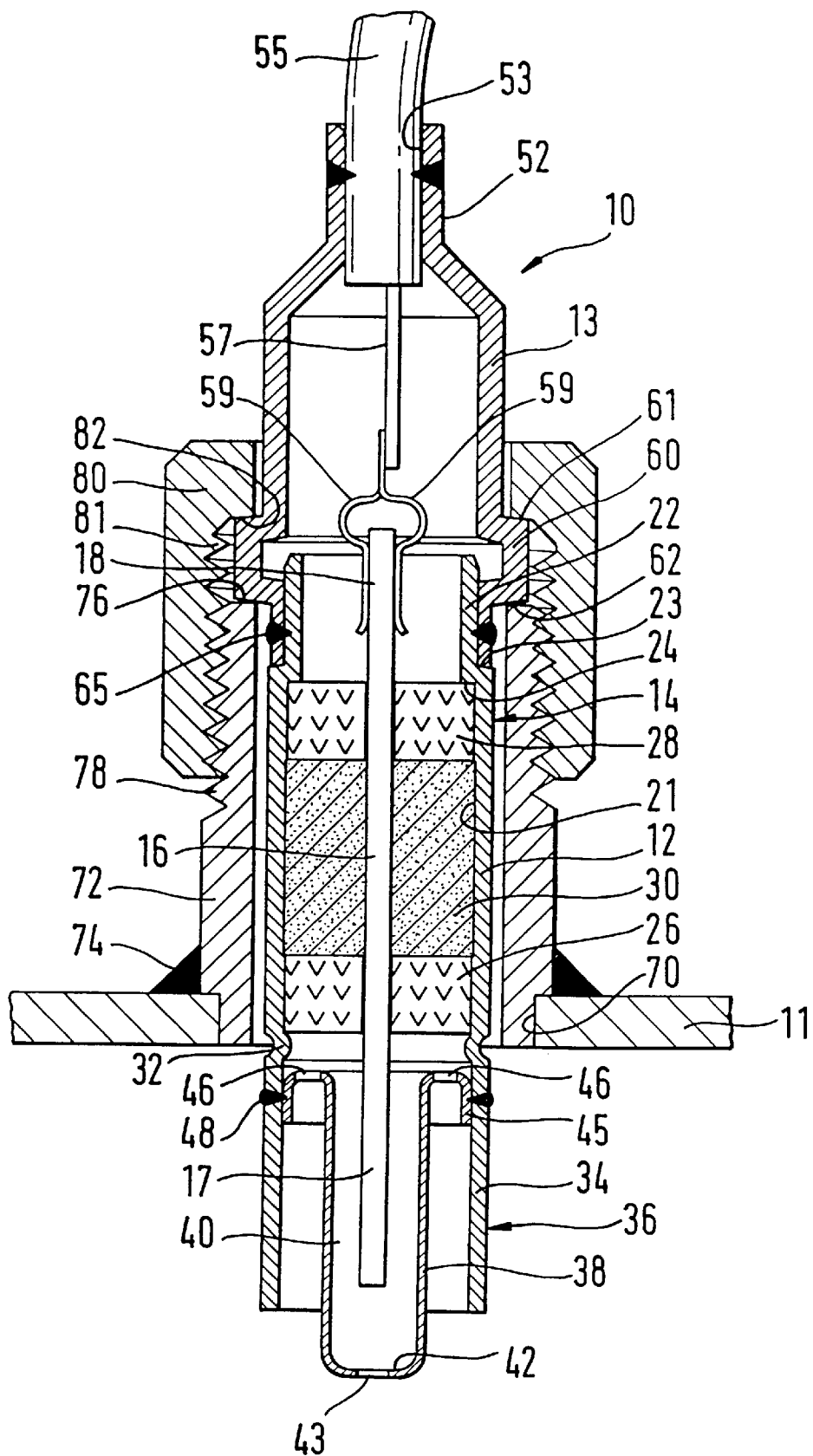

MEASURING SENSOR

PRIOR ART

The invention relates to a measuring sensor, in particular for determining the oxygen content of exhaust gases in internal combustion engines, having a sensor element fixed in a housing, a sealing flange mounted on the housing and resting on a sealing seat in an installed position, and a fastening element which is guided over and onto the housing and can be screwed into a threaded opening, with the fastening element pressing the sealing flange against the sealing seat.

From European Patent Application EP A1 624 791 (U.S. Pat. No. 5,329,806), a gas sensor is known in which a sensor element is fixed in gastight fashion in a tubular metal housing. On its lower part the tubular housing has a radially outward-pointing lip that forms a sealing flange. The gas sensor is placed in an opening of an exhaust system, with the lip seated on a sealing seat embodied in the opening. A hollow screw is guided over onto the housing and screwed into a thread disposed in the opening and thus connects the lip to the exhaust system in a gastight fashion. A problematic aspect of this embodiment, however, is that the pressing or upsetting of the relatively thin-walled material of the housing can cause microscopic cracks, which cause the housing to leak.

SUMMARY AND ADVANTAGES OF THE INVENTION

The above drawback of the known arrangements generally are overcome according to the present invention by a measuring sensor, in particular for determining the oxygen content in exhaust gases of internal combustion engines, having a sensor element fixed in a housing, a sealing flange mounted on the housing and resting on a sealing seat in an installed position, and a fastening element which is guided over and onto the housing and can be screwed into a threaded opening, with the fastening element pressing the sealing flange against the sealing seat, and wherein the housing has a housing part on the side toward the gas to be measured and a housing part on the side toward the connection, and that the sealing flange is disposed on the housing part on the side toward the connection.

The invention as defined above has the advantage over the prior art that the sealing flange is absolutely gastight. A two-piece housing with a sealing flange disposed on the housing part on the side toward the connection is not only simple to manufacture but can also be manipulated easily during assembly.

By means of other disclosed provisions advantageous further features of and improvements to the measuring sensors according to the invention as disclosed above are possible. Producing the sealing flange by the production process of rotary swaging has proved to be especially appropriate. It is also expedient to attach a connection piece to the exhaust pipe; this piece then forms a sealing seat for the sealing flange on its end face. By mounting a union nut on the sealing flange and by its cooperation with a thread provided on the connection piece, the sealing flange is joined in gastight fashion to the connection piece.

BRIEF DESCRIPTION OF THE DRAWING

An exemplary embodiment of the invention is shown in the drawing and described in further detail in the ensuing description. The sole drawing Figure is a longitudinal section through a gas sensor inserted into an exhaust pipe.

DETAILED DESCRIPTION OF THE EXEMPLARY EMBODIMENT

A gas sensor 10, such as an electrochemical oxygen sensor, is inserted into an exhaust pipe 11 and has a metal housing part 12 on the side toward the gas to be measured and a metal housing part 13 on the side toward the connection, which together form a housing 14. A planar sensor element 16 having a portion 17 on the side toward the gas to be measured and a portion 18 on the side toward the connection is fixed in the housing 14 in gastight fashion.

The housing part 12 on the side toward the gas to be measured is a tube element, for instance open on both ends, with a cylindrical wall 21 on the inside. On its end on the side toward the connection, the housing part 12 on the side toward the gas to be measured has a portion 22, for instance, of lesser outer diameter and lesser inside diameter. As a result, an outer annular face 23 and an inner annular face 24 are formed on the tube element. The housing part 12 on the side toward the gas to be measured also, for instance on its end on the side toward the gas to be measured, has a cylindrical bush 34, which extends past the end on the side toward the gas to be measured of the sensor element 16 and thereby forms an outer guard bush 36 for the portion 17 on the side toward the gas to be measured of the sensor element 16.

Disposed in the bush 34 is an inner guard bush 38, which surrounds the portion 17 on the side toward the gas to be measured of the sensor element 16 with clearance and forms a measurement gas chamber 40 in its interior. The inner guard bush 38 has a bottom 42, in which a first opening 43 is made, where gas can flow in and/or out. On the end opposite the bottom 42, the inner guard bush 38 is embodied with a flange 45, in which further openings 46 through which the gas can flow in and/or out are provided. However, it is also possible for the bush 34 to be joined as a separate part to the inner guard bush 38 and for the resultant preassembled double guard bush then to be welded, e.g., by the weld 48 to the tube element.

In the housing part 12 on the side toward the gas to be measured, there are a molded ceramic part 26 on the side toward the gas to be measured, a molded ceramic part 28 on the side toward the connection, and a sealing element 30 between them. The molded ceramic parts 26 and 28 comprise $Al_2O_3$, for example, and have leadthroughs, not identified by reference numeral, for the sensor element 16. The sealing element 30 comprises steatite, for example, and is inserted in a prepressed state in which it likewise has a leadthrough for the sensor element 16.

The fixation of the sensor element 16 in the housing part 12 on the side toward the gas to be measured is accomplished by inserting the molded ceramic part 28 on the side toward the connection, the sealing element 30 in the pressed state, and the molded ceramic part 26 on the side toward the gas to be measured into the housing part 12 on the side toward the gas to be measured in succession. The molded ceramic part 28 on the side toward the connection then rests on the inner annular face 24. The leadthroughs for the sensor element, which are not identified by reference numerals, are located in alignment one above the other. Next, the sensor element 16 is thrust through the leadthrough, until it assumes its specified axial position. Then, on the side toward the gas to be measured, a contact pressure force is exerted on the molded ceramic part 26 on the side toward the gas to be measured with a male die, the contact pressure force being dimensioned such that the prepressed sealing element 30 is crushed, causing its powdered components to press against both the sensor element 16 and the inner wall 21. During the exertion of force on the molded ceramic part 26 on the side toward the gas to be measured, a radially extending, inward-pointing indentation 32 on the end on the side toward the gas to be measured of the molded ceramic part 26 on the side toward the gas to be measured is made in the tube element. As a result, the molded ceramic part 26 on the side toward the gas to be measured is held in the compression position with respect to the sealing element 30.

The housing part 13 on the side toward the connection is embodied cylindrically and has a tapering portion 52 with an opening 53. A metal jacket tube 55, for instance, is welded into the opening 53. Connection cables 57 for the sensor element 16 are passed through the jacket tube 55. The connection cables 57 are connected to contacting elements 49, which are contacted with connection contacts, not identified by reference numeral, on the portion 18 on the side toward the connection of the sensor element 16. The contacting of the sensor element 16 can be realized for instance by clamping or by means of a materially joined connection. However, where the cable emerges through the opening 53 can also be in the form of a temperature-resistant PTFE cable leadthrough.

On the end toward the sensor element, the housing part 13 on the side toward the connection has a radially encompassing sealing flange 60, which has an upper annular face 61 and a lower annular face 62. The sealing flange 60, in the present exemplary embodiment, is formed from the material of the housing part 13 on the side toward the connection. The sealing flange 60 may be produced by various deforming processes. Rotary swaging has proved to be an especially suitable deforming process with which a stable sealing flange 60 can be shaped from the material of the housing part 13 on the side toward the connection. However, as an alternative, it is also conceivable for weld a ring onto the cylindrical housing part. 13 on the side toward the connection, and this ring then forms the sealing flange 60.

Once the sensor element 16 has been contacted with the contact elements 59, the housing part 13 on the side toward the connection is mounted on the portion 22 of the housing part 12 on the side toward the gas to be measured, with the outer annular face 23 of the housing part 12 on the side toward the gas to be measured acting as an axial stop. Next, the housing part 13 on the side toward the connection is welded gastight to the housing part 12 on the side toward the gas to be measured by means of a radially encompassing weld seam 65.

An opening 70 is provided in the exhaust pipe 11, and into it a cylindrical connection piece 72 is inserted by one end. The connection piece 72 is welded gastight to the exhaust pipe 11 by means of an encompassing weld seam 74. On its other end, the connection piece 72 has a flat annular face 76, on which the lower annular face 62 of the sealing flange 60 rests. The annular face 76 thus forms a sealing seat for the sealing flange 60. On its outer circumference, the connection piece 72 has a threaded portion 78.

A union nut 80 is guided over onto the housing part 13 on the side toward the connection by a female thread 81 and an inner annular face 82. The female thread 81 is screwed onto the threaded portion 78 of the connection piece 72, and the inner annular face 82 presses against the upper annular face 61 of the sealing flange 60. By tightening the union nut 80, the lower annular face 62 of the sealing flange 60 is pressed firmly against the annular face 76, forming the sealing seat, of the connection piece 72. This creates a gastight fastening of the gas sensor 10 in the exhaust pipe 11.

For fastening the gas sensor 10 in the exhaust pipe 11, other forms a fastening means are also possible, however. An example is fastening by means of a hollow screw, which has a thread on its outer circumference that is screwed into a female thread disposed on the connection piece 72, in which case the sealing seat for the sealing flange 60 must then be formed by an additional annular face in the interior of the connection piece 72. It is also conceivable to place an adapter between the connection piece 72 and the hollow screw; then the gas sensor 10 is seated with the sealing flange 60 on an annular face of the adapter, and the adapter rests with further annular face on the annular face of the connection piece 72.

We claim:

1. A measuring sensor for determining an oxygen content in exhaust gases of internal combustion engines comprising:

a sensor element fixed in a housing, with the housing having a measuring-gas side housing part and a connection-side housing part, with the connection-side housing part being fitted over a segment of the measuring-gas side housing part and at the fitted over segment being connected gas-tight with the measuring-gas side housing part;

a laterally extending sealing flange mounted on the connection-side housing part, with the sealing flange having an upper annular surface and a lower annular surface;

a gas tube for the gas to be measured, with the gas tube having an opening;

a connection piece that encloses the opening in the gas tube in a gas-tight manner and has one end fastened to the tube at the opening and an opposite end provided with a thread, and with the measuring-gas side housing part extending into the connection piece and through the opening into the gas pipe;

an additional annular surface formed on the connecting piece and forming a sealing seat for the lower annular surface of the sealing flange; and, a fastening element, that is separate from the housing parts, extending over the connection-side housing part and engaging the thread to fasten the housing to the connection piece, with the fastening element engaging and acting upon the upper annular surface of the sealing flange to press the lower annular surface of the sealing flange against the sealing seat of the connection piece.

2. The measuring sensor of claim 1, wherein the sealing flange is shaped from a material of the connection-side housing part.

3. The measuring sensor of claim 1 wherein the sealing flange was produced by rotary swaging.

4. The measuring sensor of claim 2, wherein the sealing flange was produced by rotary swaging.

* * * * *